US008424386B2

(12) United States Patent
Naka (10) Patent No.: US 8,424,386 B2
(45) Date of Patent: Apr. 23, 2013

(54) ULTRASONIC PROBE

(75) Inventor: Yoji Naka, Saitama (JP)

(73) Assignee: Nihon Dempa Kogyo Co., Ltd., Shibuya-Ku (JP)

( * ) Notice: Subject to any disclaimer, the term of this patent is extended or adjusted under 35 U.S.C. 154(b) by 9 days.

(21) Appl. No.: 13/199,431

(22) Filed: Aug. 30, 2011

(65) Prior Publication Data

US 2012/0073376 A1   Mar. 29, 2012

(30) Foreign Application Priority Data

Sep. 29, 2010  (JP) ................................ 2010-219215
Nov. 26, 2010  (JP) ................................ 2010-263863

(51) Int. Cl.
    *G01N 29/24*   (2006.01)

(52) U.S. Cl.
    USPC ............................................. 73/632; 73/644

(58) Field of Classification Search ............ 73/632, 73/644; 600/459; 310/334
    See application file for complete search history.

(56) References Cited

U.S. PATENT DOCUMENTS

| 7,554,245 | B2 * | 6/2009 | Hasegawa | 310/334 |
| 7,963,167 | B2 * | 6/2011 | Hasegawa | 73/632 |
| 7,967,755 | B2 * | 6/2011 | Hasegawa | 600/459 |
| 2009/0048521 | A1 * | 2/2009 | Hasegawa | 600/459 |
| 2010/0076316 | A1 * | 3/2010 | Hasegawa | 600/459 |

FOREIGN PATENT DOCUMENTS

JP   2007-222244   9/2007

* cited by examiner

*Primary Examiner* — J M Saint Surin
(74) *Attorney, Agent, or Firm* — Edwards Wildman Palmer LLP; Scott D. Wofsy; Christopher J. Capelli (57) ABSTRACT

The shapes of reflecting parts in a hermetically sealed container are inclined to prevent generation of an unnecessary echo. In a short-axis oscillating ultrasonic probe, a piezoelectric element group arranged along a long-axis direction and having an acoustic lens on an ultrasonic wave transmitting/receiving surface, is provided on a rotary holding table housed in a hermetically sealed container. An ultrasonic wave transmitted and received to/from the ultrasonic wave transmitting/receiving surface of the piezoelectric element group is mechanically scanned in the short-axis direction of the piezoelectric element group by rotating and oscillating the rotary holding table in the short-axis direction, and a liquid serving as an acoustic medium is filled in the hermetically sealed container.

2 Claims, 7 Drawing Sheets

ULTRASONIC PROBE

TECHNICAL FIELD

The present invention relates to an ultrasonic probe that transmits and receives ultrasonic waves to/from a piezoelectric element group with respect to a subject (living body), and takes in three-dimensional data for ultrasonic diagnosis of the subject. More specifically, the present invention relates to an ultrasonic probe that shields against unnecessary ultrasonic waves reflected inside a hermetically sealed container that houses the piezoelectric element group.

BACKGROUND ART

Figure 13:
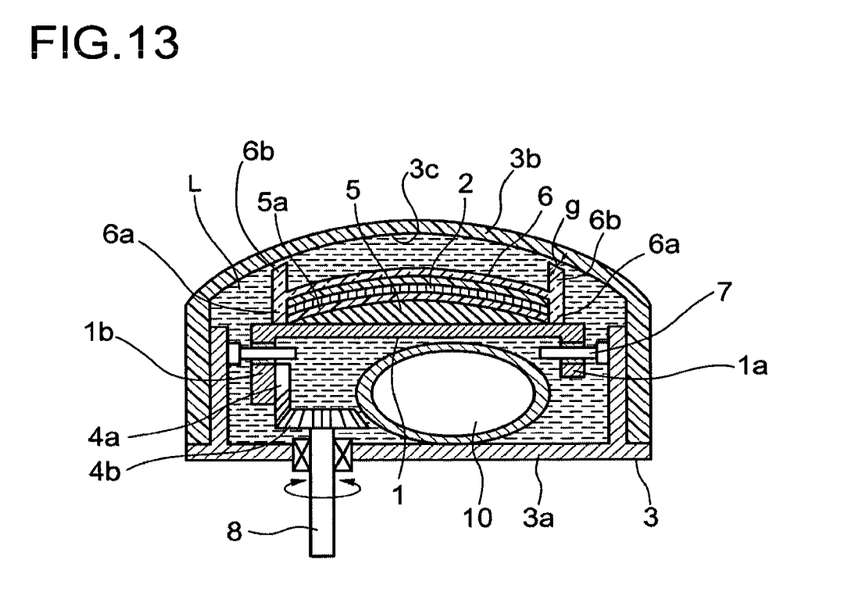
FIG. 13 is a longitudinal sectional view in the long-axis direction of the conventional ultrasonic probe.

In a conventional ultrasonic probe, for example, a short-axis oscillating ultrasonic probe, as shown in FIG. 13, a piezoelectric element group 2 arranged along a long-axis direction and having an acoustic lens 6, is provided on a horizontal part of a rotary holding table 1 and housed in a hermetically sealed container 3 including a container body 3a and a cover 3b, which each have a concave shape in cross-section. Bearings are respectively provided in legs 1a and 1b at opposite ends of the rotary holding table 1, so as to slidingly fit with central rotation shafts 7 provided on opposite side walls of the container body 3a in the long-axis direction.

A first bevel gear 4a provided at one leg 1b of the rotary holding table 1, which rotates and oscillates in the short-axis direction, is meshed with a second bevel gear 4b firmly fixed to a rotation shaft 8 sealing and penetrating a bottom wall of the hermetically sealed container 3. Accordingly, the rotary holding table 1 and the piezoelectric element group 2 are rotated and oscillated in the short-axis direction, so that ultrasonic waves transmitted and received to/from an ultrasonic wave transmitting/receiving surface of the piezoelectric element group 2 are mechanically scanned in the short-axis direction of the piezoelectric element group 2. Liquid L, serving as an ultrasonic wave medium, for example oil, is filled in the hermetically sealed container 3.

The acoustic lens 6 here has legs 6a extending from outer peripheries of a curvature portion thereof. Furthermore projecting portions 6b serving as ultrasonic wave absorbing means, are provided on the ultrasonic wave transmitting/receiving surface side at the opposite ends in the long-axis direction. Tip sides of the projecting portions 6b have a circular arc shape following an inner periphery 3c of the cover 3b. Moreover a light-weight body 10 having a hollow portion is firmly fixed to the bottom wall of the container body 3a by an adhesive or the like, and immersed in the ultrasonic wave medium L filled in below the rotary holding table 1.

According to such a configuration, because the projecting portions 6b serving as the ultrasonic wave absorbing means are provided on opposite end sides of the acoustic lens 6, unnecessary ultrasonic waves propagating in the long-axis direction of the piezoelectric element group 2 are absorbed by the ultrasonic wave absorbing means (projecting portions 6b).

PRIOR ART DOCUMENT

[Patent Document 1] Japanese Unexamined Patent Publication No. 2007-222244

SUMMARY OF THE INVENTION

Problems to be Solved by the Invention

However, in the conventional ultrasonic probe, the unnecessary ultrasonic waves that are reflected in the hermetically sealed container in which the liquid serving as the acoustic medium (ultrasonic medium) is filled, and that do not go out from the ultrasonic probe, appear as unnecessary echoes on an image of a diagnostic device, thereby disturbing ultrasonic diagnostics.

In order to prevent such unnecessary echoes, in the aforementioned Patent Document 1 (Japanese Unexamined Patent Publication No. 2007-222244), the projecting portions (ultrasonic wave absorbing means) 6b are provided on the legs of the acoustic lens. However, because a clearance g needs to be provided between the projecting portions 6b and the inner periphery 3c of the cover 3b, unnecessary echoes cannot be reduced sufficiently. Moreover the number of parts and assembly man-hours increase, thereby causing a cost increase.

Such unnecessary echoes are generated because unnecessary ultrasonic waves return to the piezoelectric element that has transmitted the ultrasonic waves in a path described below. The principles of generation of unnecessary echoes are explained with reference to FIG. 9 in the accompanying drawings.

Figure 9:
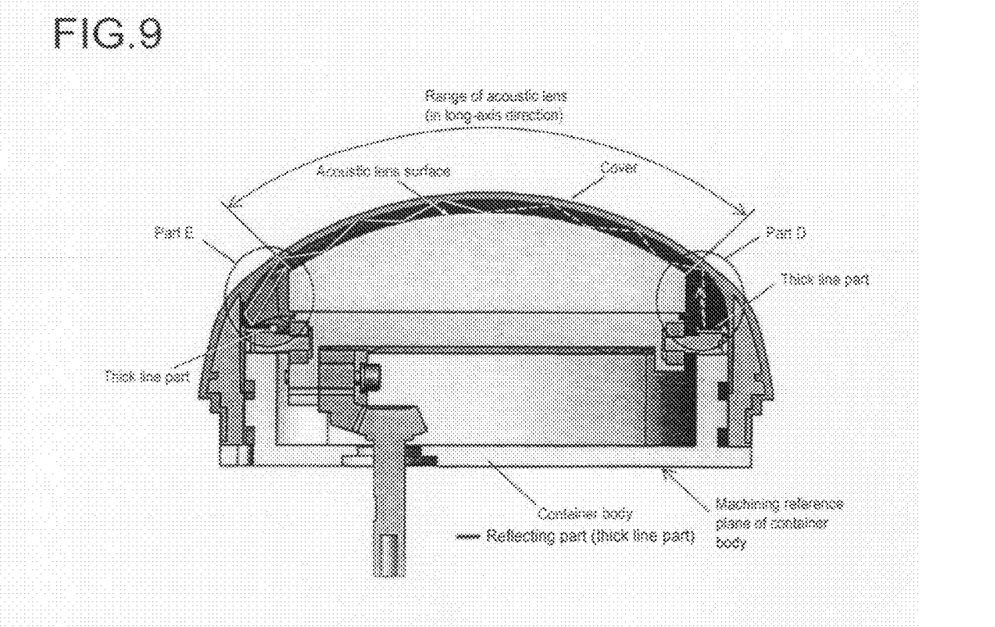
FIG. 9 is a longitudinal sectional view in a long-axis direction of the conventional ultrasonic probe shown in FIG. 8.

At first, the unnecessary ultrasonic wave radiated from the piezoelectric element is repeatedly reflected between the acoustic lens surface and the inner surface of the cover, and propagates in the long-axis or short-axis direction of the piezoelectric element group and goes outside of the range of the acoustic lens (refer to parts D and E in FIG. 9).

If at the time of being reflected by either portion in the hermetically sealed container, the unnecessary ultrasonic wave is reflected in the same direction as that before reflection, it follows the original path and finally returns to the vicinity of the point of radiation on the acoustic lens. If it is received by the piezoelectric element that has transmitted the ultrasonic wave, it becomes an unnecessary echo on the image.

Figure 10:
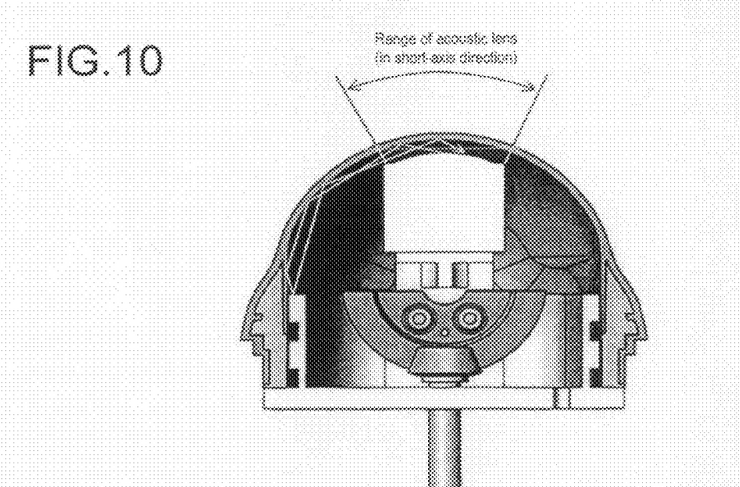
FIG. 10 is a longitudinal sectional view in a short-axis direction of the conventional ultrasonic probe shown in FIG. 8, showing a state in which the ultrasonic probe is at a central position.

The aforementioned case in which at the time of reflection the ultrasonic wave is reflected in the same direction as that before reflection and returns to the original path, is as described below. (Here, FIG. 9 shows a case in which the probe is at a central position as shown in FIG. 10, and an unnecessary ultrasonic wave propagates in the long-axis direction.)

(1) A case in which the ultrasonic wave is incident on the reflecting surface at 90 degrees (angle of incidence=0°, Part D shown in FIG. 9, shown by the dotted line in the direction of the arrow).

(2) A case in which the ultrasonic wave is incident on one of two surfaces forming an angle of approximately 90 degrees to each other (in a concave shape of a right angle corner) (Part E shown in FIG. 9, shown by the solid line in the direction of the arrow).

Figure 7:
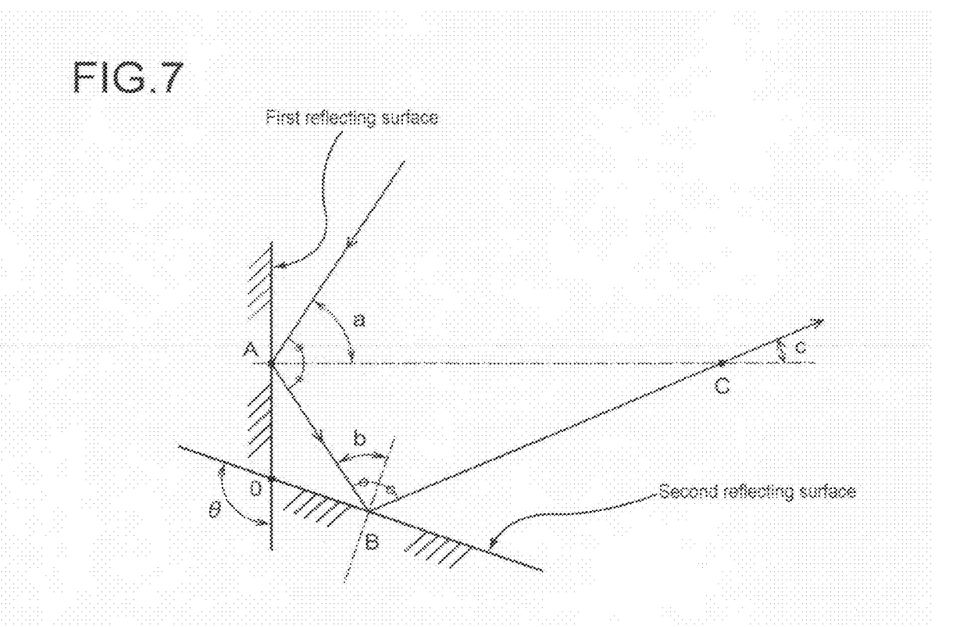
FIG. 7 shows a relation between an angle of incidence and an angle of emergence when an ultrasonic wave is reflected on two surfaces.

A supplementary explanation for (2) described above is given here. As shown in FIG. 7, when the ultrasonic wave is continuously reflected by the two surfaces (first and second reflecting surfaces) forming an angle θ to each other, a relation between the direction before reflection (angle of incidence a) and the direction after being reflected twice (angle of emergence c on the same basis) is calculated as follows, by using the property of regular reflection (values of the angle of incidence and the angle of emergence with respect to a normal to the reflecting surface are the same, and respective traveling directions before and after reflection are symmetric to the normal).

That is to say, regarding an inner angle of $\triangle ABO$ shown in FIG. 7, $$(90-a)+(90-b)+\theta=180 \rightarrow b=\theta-a$$

Furthermore, regarding the inner angle of ΔABC, a+2×b+c=180, and eliminating b gives $$c=180-a-2\times(\theta-a)=a-2\times\theta+180$$

and when θ=90, c=a.

Accordingly, in the case of θ=90°, the angle of emergence is the same as the angle of incidence for any angle of incidence, and because the angle a and the angle c are here defined to be in the same direction with respect to the reference, the traveling direction before and after reflection becomes the same.

Therefore, for any incidence angle, the ultrasonic wave returns to the original path after reflection, and hence, it can be seen that the continuous reflection on the two surfaces forming 90 degrees is likely to cause an unnecessary echo.

An example in which the unnecessary ultrasonic wave returns to the piezoelectric element due to the reflection on each reflecting part is explained next.

FIG. 10 shows a case in which the probe is at the central position, and an unnecessary ultrasonic wave propagates in the short-axis direction.

Figure 11:
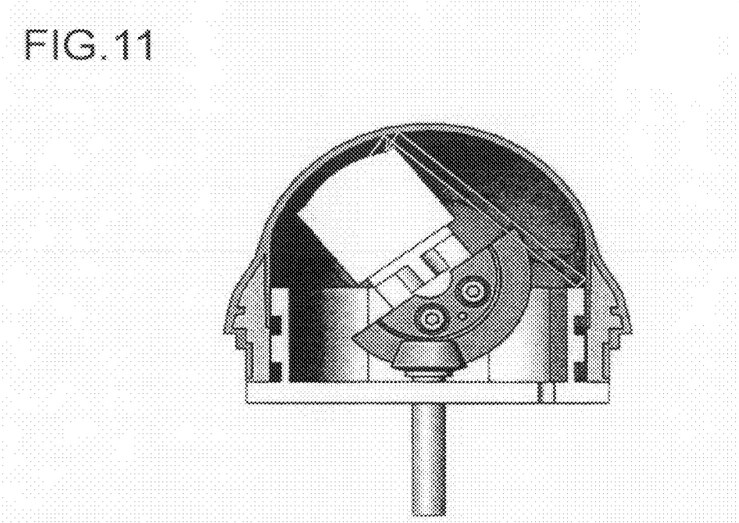
FIG. 11 shows a position at which the conventional ultrasonic probe shown in FIG. 8 is turned by a predetermined angle in the short-axis direction.

FIG. 11 shows a case in which the probe is at a position turned by a predetermined angle, and an unnecessary ultrasonic wave propagates in the short-axis direction.

FIG. 10 and FIG. 11 both show a situation in which an upper end face (face U shown in FIG. 8) of the container body and the inner periphery of the cover constitute two surfaces forming 90 degrees to each other, and an unnecessary ultrasonic wave reflected on this part returns to the path before reflection.

Figure 8:
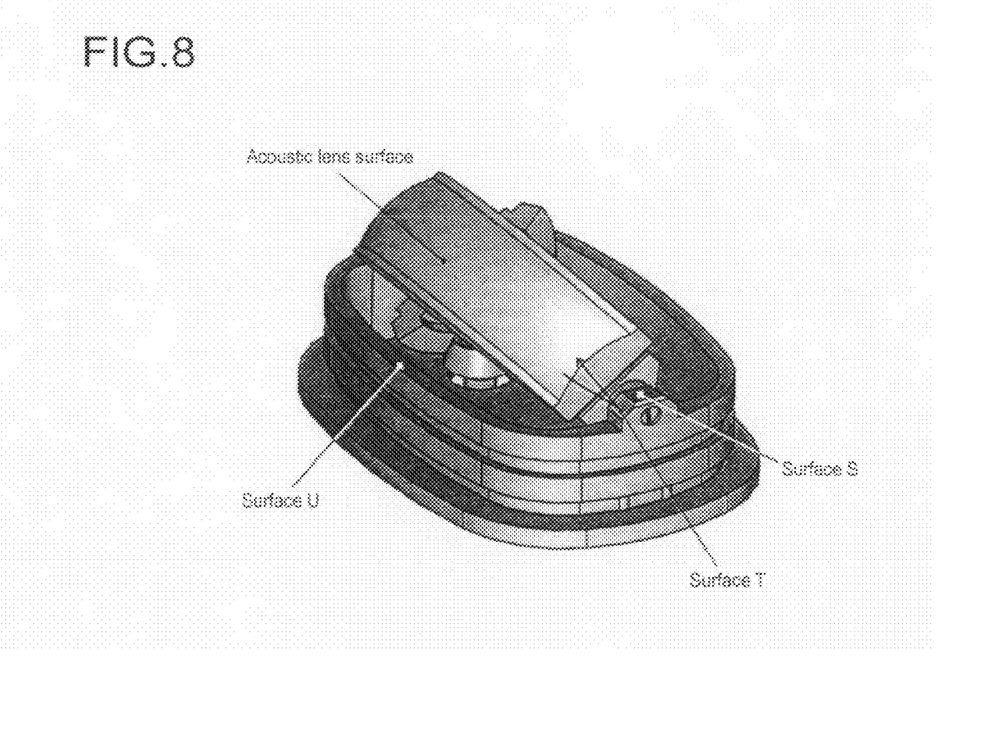
FIG. 8 is a perspective view of a conventional ultrasonic probe as seen from above, with a cover being detached.

The arrow (arrow of solid line) shown in FIG. 8 indicates a situation in which when the probe is at the turned position and the unnecessary ultrasonic wave propagates in the long-axis direction, the unnecessary ultrasonic wave is reflected by an end face of the container body (face T shown in FIG. 8). Here the angle of incidence of the unnecessary ultrasonic wave on the face T is approximately 0°. Therefore, as in the reflection on the part D shown in FIG. 9, the direction after reflection becomes approximately the same as that before reflection, and the unnecessary ultrasonic wave returns to the original path.

Moreover, the configuration of the reflecting part is explained.

As described above, the faces S, T, and U shown in FIG. 8 are end faces of the container body, and the face S and face U are formed to be parallel with a machining reference plane shown in FIG. 9, so that component manufacturing becomes easy. Moreover, because the inner face of the cover is fitted to the container body, the inner face becomes a face approximately perpendicular to the faces S, T, and U of the container body at portions adjacent to these faces.

Means for Solving the Problems

In order to solve the aforementioned problems, in a short-axis oscillating ultrasonic probe of the present invention, in order to prevent generation of an unnecessary echo, there is constructed a short-axis oscillating ultrasonic probe in which a piezoelectric element group arranged along a long-axis direction and having an acoustic lens on an ultrasonic wave transmitting/receiving surface, is provided on a rotary holding table housed in a hermetically sealed container, and an ultrasonic wave transmitted and received to/from an ultrasonic wave transmitting/receiving surface of the piezoelectric element group is mechanically scanned in a short-axis direction of the piezoelectric element group by rotating and oscillating the rotary holding table in the short-axis direction, and liquid serving as an acoustic medium is filled in the hermetically sealed container. Surface shapes of reflecting parts in the hermetically sealed container are inclined so that, when an unnecessary ultrasonic wave traveling in the hermetically sealed container and exceeding a range of the acoustic lens after propagating in the long-axis direction or the short-axis direction between the surface of the acoustic lens and the inner periphery of the hermetically sealed container, is reflected on any of the reflecting parts, the unnecessary ultrasonic wave after being reflected does not return to between a surface of the acoustic lens and an inner periphery of the hermetically sealed container.

Moreover, in the ultrasonic probe of the present invention, the hermetically sealed container comprises a cover that comes in contact with the body surface of a subject at least at the time of ultrasonic diagnostics, and a container body that supports the rotary holding table. Furthermore, the reflecting part comprises a part of a face of the container body. A face of the reflecting part is inclined so that an angle of incidence on the reflecting part of the unnecessary ultrasonic wave traveling toward the reflecting part becomes as large as possible, so that the unnecessary ultrasonic wave after being reflected on the reflecting part, travels in a direction different from the traveling direction before reflection.

Moreover, in the ultrasonic probe of the present invention, the hermetically sealed container comprises a cover that comes in contact with the body surface of a subject at least at the time of ultrasonic diagnostics, and a container body that supports the rotary holding table. Furthermore, the reflecting part comprises two faces, that is, a part of an inner periphery of the cover and a part of the face of the container body adjacent thereto. One of the two faces or both faces are inclined so that an angle formed by the two faces becomes an acute angle or an obtuse angle, so that the unnecessary ultrasonic wave, after being reflected continuously on the two faces, travels in a direction different from the traveling direction before reflection.

Effects of the Invention

The surface shape of the reflecting part is inclined so that when the unnecessary ultrasonic wave traveling in the hermetically sealed container is reflected on either one reflecting part in the hermetically sealed container, the unnecessary ultrasonic wave after reflection is not reflected in a direction returning to between the surface of the acoustic lens and the inner periphery of the hermetically sealed container, thereby preventing generation of an unnecessary ultrasonic wave. Therefore, even if the probe is at the central position or at the turned position, the generation of unnecessary echoes which are generated in the conventional probe, can be prevented, and an excellent ultrasonic image can be obtained (refer to the column for the probe of the present invention in FIG. 12).

BEST MODE FOR CARRYING OUT THE INVENTION

In the short-axis oscillating ultrasonic probe of the present invention, the shape of a reflecting part of a hermetically sealed container in which reflection described above occurs, is such that an ultrasonic wave after reflection does not return to a traveling direction before reflection. Therefore, as a point to be solved of the present invention:

(1) reflecting surfaces are inclined so that for all unnecessary ultrasonic waves entering into a reflecting surface of the reflecting part, an angle between the reflecting surfaces does not become 90 degrees (an angle of incidence of 0°), and (2) when the shape of the reflecting part comprises two surfaces (first and second reflecting surfaces), one or both reflecting surfaces is/are inclined so that the angle formed by the two surfaces does not become 90 degrees.

Therefore, in the short-axis oscillating ultrasonic probe of the present invention, as shown in FIG. 1 to FIG. 5, in order to prevent generation of an unnecessary echo, a piezoelectric element group 2 arranged along a long-axis direction and having an acoustic lens 6 on an ultrasonic wave transmitting/receiving surface, is provided on a rotary holding table 1 housed in a hermetically sealed container 3, and the rotary holding table 1 is rotated and oscillated in a short-axis direction of the piezoelectric element group 2 by a rotation shaft 8, a first bevel gear 4a, and a second bevel gear 4b. Accordingly, there is constructed an ultrasonic probe in which an ultrasonic wave transmitted and received to/from the ultrasonic wave transmitting/receiving surface of the piezoelectric element group 2 is mechanically scanned in the short-axis direction, and a liquid L serving as an acoustic medium is filled in the hermetically sealed container 3. The surface shapes of the reflecting parts in the hermetically sealed container are inclined so that, when an unnecessary ultrasonic wave travelling in the hermetically sealed container 3 and exceeding a range of the acoustic lens 6 after propagating in the long-axis direction or the short-axis direction between the surface of the acoustic lens 6 and the inner periphery 3c of the hermetically sealed container 3, is reflected on any of the reflecting parts, the unnecessary ultrasonic wave after being reflected does not return to between a surface of the acoustic lens 6 and an inner periphery 3c of the hermetically sealed container 3.

Moreover, in the ultrasonic probe of the present invention, the hermetically sealed container 3 comprises a cover 3b that comes in contact with the body surface of a subject at least at the time of diagnosis, and a container body 3d that supports the rotary holding table 1. Furthermore, the reflecting part comprises a part of the face of the container body 3d. The face of the reflecting part is inclined so that the angle of incidence on the reflecting part of the unnecessary ultrasonic wave travelling toward the reflecting part becomes as large as possible, so that the unnecessary ultrasonic wave after being reflected on the reflecting part, travels in a direction different from the traveling direction before reflection.

Moreover, in the ultrasonic probe of the present invention, the hermetically sealed container 3 comprises the cover 3b that comes in contact with the body surface of a subject at least at the time of diagnosis, and the container body 3d that supports the rotary holding table 1. Furthermore, the reflecting part comprises two faces, that is, a part of the inner periphery of the cover 3b and a part of the face of the container body 3d adjacent thereto. One of the two faces or both faces are inclined so that an angle formed by the two faces becomes an acute angle or an obtuse angle, so that the unnecessary ultrasonic wave, after being reflected continuously on the two faces, travels in a direction different from the traveling direction before reflection.

Figure 1:
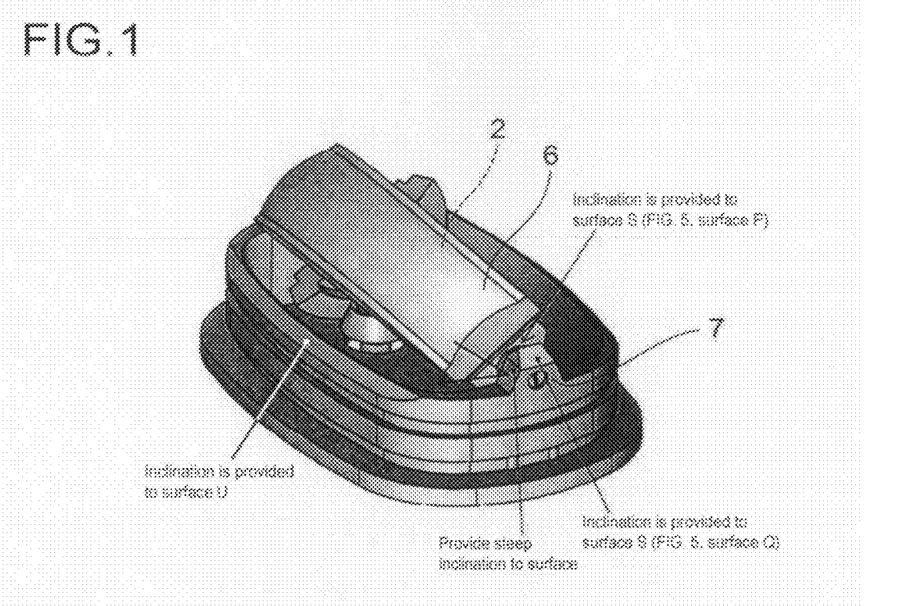
FIG. 1 is a perspective view of an ultrasonic probe of the present invention as seen from above, with a cover being detached.

Inclinations as shown in FIG. 1 are provided to the respective surfaces S, T, and U having conventional shapes shown in FIG. 8.

Point (1) of the present invention is explained first.

Figure 5:
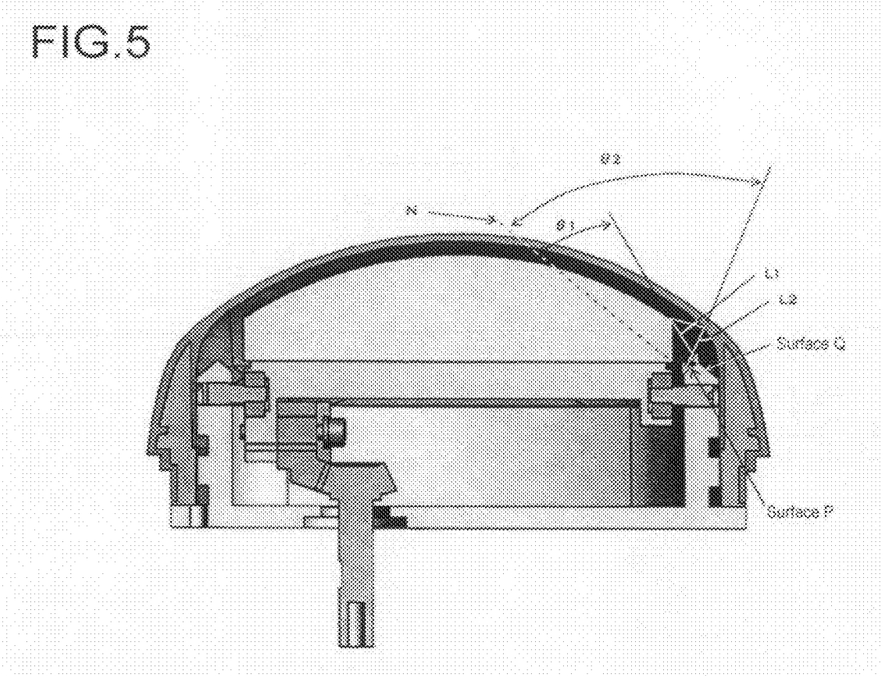
FIG. 5 shows an inclined surface of an acoustic lens of the ultrasonic probe of the present invention shown in FIG. 1.

An inclined surface is provided on a surface P, as shown in FIG. 5, with respect to the surface S of the conventional probe shown in FIG. 8. Accordingly, the range of the angle of incidence of the ultrasonic wave entering into the surface P has two maximal ranges described below. That is;

Ultrasonic wave coming from the leftmost side with respect to the surface P=ultrasonic wave radiated from near the end of the acoustic lens and traveling directly toward the right end of the surface P (refer to L1 in FIG. 5).

Ultrasonic wave coming from the rightmost side with respect to the surface P=ultrasonic wave radiated from near the end of the acoustic lens, reflected on the inner periphery of the cover, and traveling toward the left end of the surface P (refer to L2 in FIG. 5).

Here, a normal N of the surface P is not included in the range of directions of L1 and L2, and hence, the unnecessary ultrasonic wave having propagated in the long-axis direction of the piezoelectric element group is not reflected at an angle of incidence 0°, and the reflected ultrasonic wave does not return to the original path.

Figure 6:
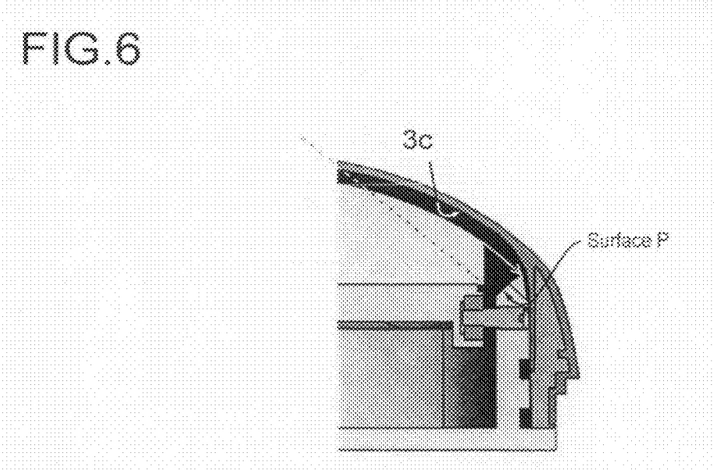
FIG. 6 shows a state in which a surface P shown in FIG. 5 is extended up to a cover that comes in contact with a body surface of a subject.

Moreover, when the surface P shown in FIG. 5 is extended up to the inner periphery of the cover, as shown in FIG. 6, some of the ultrasonic waves traveling toward the surface P become parallel to the normal to the surface P (an angle of incidence 0°), thereby generating unnecessary ultrasonic waves. Therefore, in the present invention, the surface P is inclined in a direction opposite to the surface P without extending the surface P to the inner periphery of the cover, to form a surface Q as shown in FIG. 5.

Furthermore, point (2) of the present invention is explained below.

For the surface Q shown in FIG. 5, an angle with the inner periphery of the cover near the surface Q is about 45 degrees.

Figure 2:
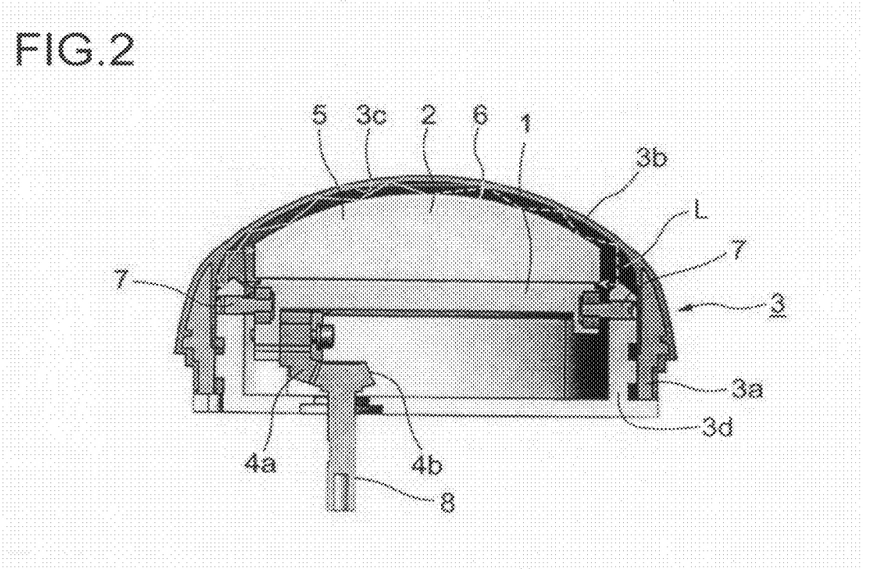
FIG. 2 is a longitudinal sectional view in a long-axis direction of the ultrasonic probe of the present invention shown in FIG. 1.

Therefore, even if the ultrasonic wave is repeatedly reflected on these surfaces, the ultrasonic wave travels in a direction different from that before reflection, and hence, the ultrasonic wave does not return to the original path (refer to the solid line shown by the left arrow in FIG. 2).

Moreover, reflection on the respective reflecting parts is explained.

Figure 3:
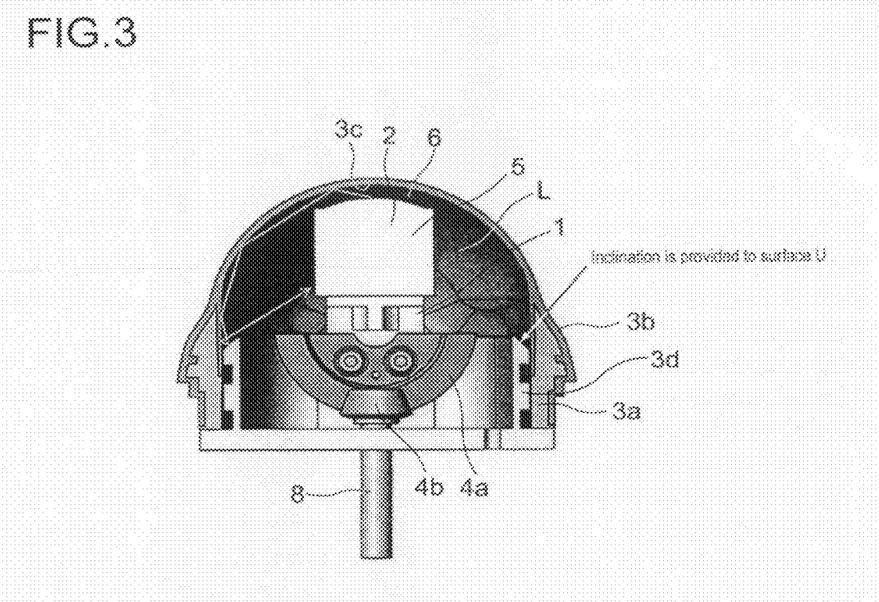
FIG. 3 is a longitudinal sectional view in a short-axis direction of the ultrasonic probe of the present invention shown in FIG. 1, showing a state in which the ultrasonic probe is at a central position.

FIG. 3 shows a result of providing an inclined surface on the surface U at the upper end of an inner cylinder 3d of the container body, when the probe is at the central position and an unnecessary ultrasonic wave propagates in the short-axis direction.

Figure 4:
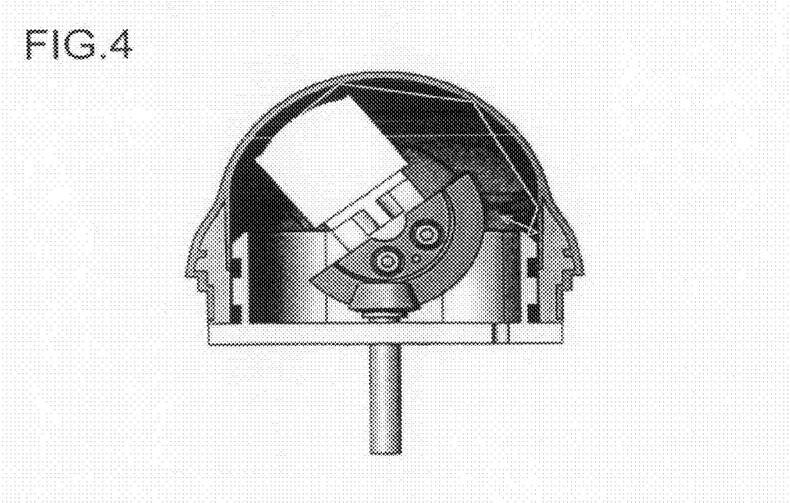
FIG. 4 shows a position at which the ultrasonic probe of the present invention shown in FIG. 3 is turned by a predetermined angle in the short-axis direction.

FIG. 4 shows a result of providing an inclined surface on the surface U when the probe is at a position turned by a predetermined angle and an unnecessary ultrasonic wave propagates in the short-axis direction.

In the probe shown in FIG. 3 and FIG. 4, both the surface U and the inner periphery of the cover form the two faces forming an angle of about 45 degrees to each other, and the unnecessary ultrasonic wave reflected on the reflecting part travels in a direction different from that before reflection.

Here, the arrow shown in FIG. 1 indicates a result of providing a steep inclination on the surface T, when the probe is at the position turned by the predetermined angle and the unnecessary ultrasonic wave propagates in the long-axis direction. By having such a shape, the angle of incidence of the unnecessary ultrasonic wave on the surface T is not 0°, and hence, the unnecessary ultrasonic wave does not return to the path before reflection.

An effect in an image of a diagnostic device that uses the ultrasonic probe of the present invention is explained next.

Figure 12:
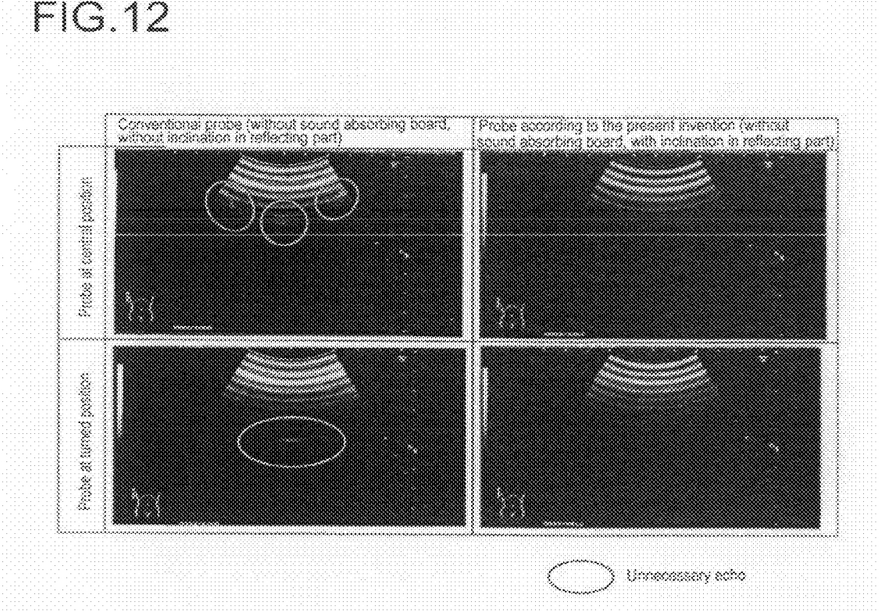
FIG. 12 is photographs showing an image of a diagnostic device using the conventional ultrasonic probe and a diagnostic device using the ultrasonic probe of the present invention.

As seen in the images shown in FIG. 12, in the ultrasonic probe (probe) of the present invention, even when the probe is at the central position or at the turned position, unnecessary echoes, which have been generated in the conventional ultrasonic probe, are not generated, and excellent images suitable for ultrasonic diagnostics can be obtained.

That is, as shown in FIG. 12, in the conventional probe, unnecessary echoes are generated at three positions in the oscillation direction as shown by the circles when the probe is at the central position, and an unnecessary echo is generated at about the rotational center when the probe is at the position turned by the predetermined angle. However, in the probe of the present invention, there is no generation of unnecessary echoes.

What is claimed is:

1. A short-axis oscillating ultrasonic probe in which a piezoelectric element group arranged along a long-axis direction and having an acoustic lens on an ultrasonic wave transmitting/receiving surface, is provided on a rotary holding table housed in a hermetically sealed container, and an ultrasonic wave transmitted and received to/from an ultrasonic wave transmitting/receiving surface of said piezoelectric element group is mechanically scanned in a short-axis direction of said piezoelectric element group by rotating and oscillating said rotary holding table in said short-axis direction, and a liquid serving as an acoustic medium is filled in said hermetically sealed container, wherein surface shapes of reflecting parts in the hermetically sealed container are inclined so that, when an unnecessary ultrasonic wave traveling in said hermetically sealed container and exceeding a range of said acoustic lens after propagating in the long-axis direction or the short-axis direction between the surface of said acoustic lens and the inner periphery of said hermetically sealed container, is reflected on any of said reflecting parts, the unnecessary ultrasonic wave after being reflected does not return to between a surface of said acoustic lens and an inner periphery of said hermetically sealed container;

wherein said hermetically sealed container comprises a cover that comes in contact with the body surface of a subject at least at the time of ultrasonic diagnostics, and a container body that supports said rotary holding table, and said reflecting part comprises a part of a face of said container body, and a face of said reflecting part is inclined so that an angle of incidence on said reflecting part of said unnecessary ultrasonic wave traveling toward said reflecting part becomes as large as possible, so that said unnecessary ultrasonic wave after being reflected on said reflecting part, travels in a direction different from the traveling direction before reflection.

2. A short-axis oscillating ultrasonic probe in which a piezoelectric element group arranged along a long-axis direction and having an acoustic lens on an ultrasonic wave transmitting/receiving surface, is provided on a rotary holding table housed in a hermetically sealed container, and an ultrasonic wave transmitted and received to/from an ultrasonic wave transmitting/receiving surface of said piezoelectric element group is mechanically scanned in a short-axis direction of said piezoelectric element group by rotating and oscillating said rotary holding table in said short-axis direction, and a liquid serving as an acoustic medium is filled in said hermetically sealed container, wherein surface shapes of reflecting parts in the hermetically sealed container are inclined so that, when an unnecessary ultrasonic wave traveling in said hermetically sealed container and exceeding a range of said acoustic lens after propagating in the long-axis direction or the short-axis direction between the surface of said acoustic lens and the inner periphery of said hermetically sealed container, is reflected on any of said reflecting parts, the unnecessary ultrasonic wave after being reflected does not return to between a surface of said acoustic lens and an inner periphery of said hermetically sealed container;

wherein said hermetically sealed container comprises a cover that comes in contact with the body surface of a subject at least at the time of ultrasonic diagnostics, and a container body that supports said rotary holding table, and said reflecting part comprises two faces, that is, a part of an inner periphery of said cover and a part of the face of said container body adjacent thereto, and one of said two faces or both faces are inclined so that an angle formed by said two faces becomes an acute angle or an obtuse angle, so that said unnecessary ultrasonic wave, after being reflected continuously on said two faces, travels in a direction different from the traveling direction before reflection.

* * * * *